United States Patent [19]
Gross

[11] Patent Number: 5,814,020
[45] Date of Patent: Sep. 29, 1998

[54] MEDICAMENT DELIVERY DEVICE

[75] Inventor: Joseph Gross, Dublin, Ireland

[73] Assignee: Elan Medical Technlogies Limited, Athlone, Ireland

[21] Appl. No.: 708,230

[22] Filed: Sep. 6, 1996

[30] Foreign Application Priority Data

Sep. 11, 1995 [IE] Ireland ..................................... 950702

[51] Int. Cl.⁶ ................................................. A61M 37/00
[52] U.S. Cl. ............................................. 604/41; 604/151
[58] Field of Search ............................. 604/83–89, 131, 604/132, 133, 141, 142, 145, 146, 147, 151, 153, 156, 157, 140

[56] References Cited

U.S. PATENT DOCUMENTS

| | | | |
|---|---|---|---|
| 2,408,323 | 9/1946 | Lockhart et al. | 128/220 |
| 2,576,951 | 12/1951 | Lockhart et al. | 128/218 |
| 3,923,060 | 12/1975 | Ellinwood | 128/260 |
| 4,034,756 | 7/1977 | Higuchi et al. | 128/260 |
| 4,180,070 | 12/1979 | Genese | 128/218 M |
| 4,522,622 | 6/1985 | Peery et al. | 604/191 |
| 4,627,445 | 12/1986 | Garcia et al. | 128/770 |
| 4,637,403 | 1/1987 | Garcia et al. | 128/770 |
| 4,684,365 | 8/1987 | Reinicke | 604/126 |
| 4,697,622 | 10/1987 | Swift et al. | 141/1 |
| 4,753,651 | 6/1988 | Eckenhoff | 424/449 |
| 4,886,499 | 12/1989 | Cirelli et al. | 604/131 |
| 4,894,054 | 1/1990 | Miskinyar | 604/136 |
| 4,902,278 | 2/1990 | Maget et al. | 604/132 |
| 5,070,886 | 12/1991 | Mitchen et al. | 128/771 |
| 5,079,421 | 1/1992 | Knudson et al. | 250/343 |
| 5,122,116 | 6/1992 | Kriesel et al. | 604/89 |
| 5,328,464 | 7/1994 | Kriesel et al. | 604/83 |
| 5,336,180 | 8/1994 | Kriesel et al. | 604/82 |
| 5,336,188 | 8/1994 | Kriesel | 604/132 |
| 5,390,671 | 2/1995 | Lord et al. | 128/635 |
| 5,411,480 | 5/1995 | Kriesel | 604/133 |
| 5,419,771 | 5/1995 | Kriesel | 604/132 |
| 5,492,534 | 2/1996 | Athayde et al. | 604/141 |
| 5,514,090 | 5/1996 | Kriesel et al. | 604/85 |
| 5,545,143 | 8/1996 | Fischell | 604/180 |
| 5,562,613 | 10/1996 | Kaldany | 604/57 |
| 5,656,032 | 8/1997 | Kriesel et al. | 604/132 |

FOREIGN PATENT DOCUMENTS

| | | |
|---|---|---|
| 0 098 592 | 1/1984 | European Pat. Off. ......... A61M 5/00 |
| 0 209 677 | 1/1987 | European Pat. Off. ......... A61M 5/14 |
| 0 401 179 | 12/1990 | European Pat. Off. ......... A61B 5/00 |
| WO 91/00753 | 1/1991 | WIPO ............. A61M 31/00 |
| WO 92/11879 | 7/1992 | WIPO ............. A61M 1/08 |
| WO 95/10223 | 4/1995 | WIPO ............. A61B 5/00 |
| WO 95/13838 | 5/1995 | WIPO ............. A61M 5/142 |
| WO 96/25089 | 8/1996 | WIPO ............. A61B 5/00 |

OTHER PUBLICATIONS

Derwent Abstract No. 78–25573 A for DE 2643946; Title= "Biological fuel cell for heart pace makers etc.–in which the membrane and electrodes are compressed together by e.g. a swellable copolymer gel".

Primary Examiner—Wynn Wood Coggins
Assistant Examiner—Deborah Blyveis
Attorney, Agent, or Firm—Kathleen L. Maher

[57] ABSTRACT

A medicament delivery device has a reservoir within a housing and means for driving medicament from the reservoir. The device is provided with a filling mechanism upon which a medicament container sealed by a penetrable stopper is mounted. The mechanism comprises an internal bore which accommodates an internal rod from which a needle projects. Needle is hollow and is in communication with the reservoir. In order to fill the reservoir, the container is pressed into the bore, causing the needle to pierce the stopper, the stopper abutting against the rod and acting as a piston to drive medicament from the container as the container is pushed into the bore and moves relative to the stopper. Thus, the reservoir can be filled with the sterile medicament which is stable when stored in the container, and the filling is easily accomplished without the use of a syringe. A further advantageous feature is provided by a delivery needle which is mounted on the periphery of the lower surface of the housing. This configuration allows the driving means to be located adjacent to the skin, thereby, providing a more stable temperature and more predictable operation of the device.

63 Claims, 6 Drawing Sheets

MEDICAMENT DELIVERY DEVICE

FIELD OF THE INVENTION

This invention relates to medicament delivery devices for the delivery of pharmacological, biological and nutritive substances to a human or animal, in the form of a liquid, solution, suspension or other flowable form such as a flowable gel.

BACKGROUND OF THE INVENTION

Medicament delivery devices for delivering medicaments to a patient generally comprise a reservoir for the medicament and means for delivering the medicament to the patient. The reservoir can be pre-filled with a medicament, or the device can be provided with means for filling the reservoir. Typically, such means may be a self-sealing plug which can be pierced with a syringe allowing the medicament to be injected into the reservoir.

There is concern in relation to pre-filled medicament delivery devices regarding the stability and storage characteristics of the medicament within the reservoir. Regulatory authorities are reluctant to approve products having a potentially long shelf residence if the medicament is stored in, for example, an elastomeric reservoir (many devices have a reservoir bounded, in part, by a flexible diaphragm which is used to compress and deliver the medicament). Generally, drugs are likely to be more stable and regulatory approval is easier to obtain if the drugs are stored in glass, as is traditional with medicament vials. Furthermore, some drugs are unstable when stored in liquid form and thus require reconstitution, dilution or dissolution from a solid or semi-solid form prior to use.

If the reservoir is intended to be filled prior to use, and if self-administration by the patient is desired, there may be concerns over a patient filling the reservoir where a syringe is used for this purpose, for reasons of safety, incorrect dosage or procedural error.

The present invention seeks to address these problems and to provide a means of storing medicaments in a stable condition over extended periods of time and subsequently filling such a device for delivery of the medicament easily, quickly and safely.

Another problem associated with medicament delivery devices concerns the rate of delivery of medicament therefrom. Generally, a driving means is employed to deliver medicament from the reservoir after the reservoir has been filled. A presently preferred driving means employs a gas generator such as an electrolytic cell to generate a gas and push medicament from the reservoir. This type of driving means may be preferred because of its reliable and controllable delivery rate. It is often the case, however, that variations in temperature affect the rate of gas generation and the volume of gas already generated (and the same may be true of other driving means as well). Accordingly, the invention seeks to provide an arrangement which minimises variations in delivery rate arising from environmental temperature variations.

A further object of the invention is the provision of a device which is easier to apply to the skin than prior art devices such as the devices disclosed in our U.S. Pat. No. 5,527,288 and U.S. Ser. No. 08/647,954, which references are hereby incorporated by reference. U.S. Ser. No. 08/647,954 employs a movable cover which snaps from a position where the needle is concealed to a position where the needle is exposed. The cover is placed against (and adheres to) the skin and then the device is pressed onto the skin, causing the device to snap onto the cover, the needle penetrating the skin through an aperture disposed centrally of the cover. Whereas this arrangement has a number of advantages, including the safety feature inherent in having a needle protected by a movable cover, the needle only being exposed when the cover is snapped upwards relative to the device, a good deal of force may be required to snap the device onto the cover.

A further object of the invention is to provide a device which gives a visual indication of the level of medicament remaining for delivery, as this allows the patient or physician to replace the device as soon as delivery is completed, if necessary.

Devices which are to be worn adjacent to the skin are unsuitable for use with certain medicaments, as some medicaments (such as many polypeptides) are unstable at temperatures as low as body temperature over extended periods of time.

SUMMARY OF THE INVENTION

The invention provides a medicament delivery device comprising a housing, a reservoir within the housing, a filling mechanism for the reservoir integral with the housing and means for driving the medicament from the filled reservoir, the filling mechanism being adapted to receive a container for the medicament, said container being sealed by a penetrable stopper, and the filling mechanism comprising means for penetrating the stopper, said penetrating means being in communication with the reservoir to allow the medicament to be transferred from the container to the reservoir via the filling mechanism.

It will be appreciated that such a device allows medicament stored in a container such as a vial or ampoule to be loaded directly into the delivery device without the use of a syringe, thereby eliminating concerns over patient error in filling the reservoir while also allowing the medicament to be stored for an extended period prior to use in a sterile condition.

Preferably, the container is capable of sliding within the housing, and the stopper makes a leakproof sliding fit with the interior of the container.

Further, preferably, the housing is provided with a bore which receives the container and the penetrating means is disposed on a stop within the bore, such that the stopper is penetrated and abuts against the stop when the container is pushed along the bore, the penetrated stopper acting as a piston to deliver the medicament from the container.

Thus, the penetrating means can be recessed within the housing, avoiding the risk of injury to the person filling the device, or subsequent injury when the device is disposed of. The act of filling the device is extremely simple, merely requiring the container to be pushed along the bore. This act causes the penetration of the stopper and the expulsion of the contents of the container via the aperture created in the stopper by the penetrating means. As the medicament is sealed within the container until the stopper is penetrated and as no outside agency is used to transfer the medicament to the reservoir, sterility can be ensured. This is not the case where a syringe must be used to extract medicament from a vial or ampoule and subsequently inject the medicament into a reservoir.

The reference to a piston-like action means simply that the stopper moves relative to the container (i.e. the stopper can be held in position and the container can be moved, unlike a regular piston which moves as the cylinder remains stationary).

According to a preferred embodiment, the penetrating means comprises a hollow needle and the stop is a rod extending within the bore, the needle communicating with the reservoir via a conduit extending internally of the rod.

A hollow needle communicating with the reservoir via a conduit is particularly suitable as it allows easy penetration and transfer of medicament to the reservoir. The rod extending within the bore provides a structure which allows transfer of medicament via the internal conduit, and which allows a container such as a cylindrical vial to be pushed along the bore, the rod being accommodated inside the cylinder as the cylinder empties.

Preferably, the container protrudes from the housing prior to use and moves to a recessed position within the housing when the reservoir is filled with the medicament.

This arrangement is particularly suitable as it allows for easy disposal of the entire device, including the container which does not have to be disposed of separately. This is particularly important as the disposal of containers containing even small amounts of potent medicaments is an obvious health hazard if children might obtain access to the containers after disposal. This may happen, for example, where the delivery device is used for self-administration by patients at home.

The arrangement further reduces any possibility of incorrect filling of the reservoir, as the container which protrudes from the device merely has to be pushed home to a recessed position within the housing to ensure that the reservoir is correctly filled.

In a preferred embodiment, the container is integral with the housing.

This embodiment is particularly preferred in many applications for reasons of hygiene and sterility. By mounting the container on the housing during assembly, and preferably making the container an integral part of the device, a sealed assembly is provided which can be designed to eliminate any possibility of contamination or tampering with the medicament. Thus, one can obtain a device which is effectively marketable as a pre-filled device, but which eliminates concerns over the conditions under which the medicament is stored during the shelf-life of the device.

Alternatively, in suitable circumstances, the container is separate from the housing and is mounted thereon prior to use.

This embodiment may be more suitable if the device (other than the container) is to be sold as a general purpose medicament delivery device, with a range of medicament types and strengths available for use with the device.

This option also allows the use of a reconstitutable or soluble medicament which can be stored in a container in solid form, and reconstituted or dissolved immediately prior to use, and the container can then be fitted to the housing and the medicament added to the reservoir. While such an arrangement may not be as inherently hygenic as a sealed assembly, it nevertheless offers the possibility of a safe, accurate and reliable filling mechanism for use with medicaments which would otherwise be unstable if stored in a medicament delivery device. It may be the case that where a solid or semi-solid medicament is stored in a sealed container, and is subsequently reconstituted, diluted or suspended, that the stopper is pierced during the addition of the liquid medium, at which point it is provided with a small hole. In such circumstances, however, the container is still to be regarded as a container "sealed" by a penetrable stopper.

Accordingly, the invention encompasses the device on its own, when supplied without the container (but the filling mechanism is adapted to received a container which is sealed by a penetrable stopper).

Suitably, the penetrating means penetrates partially into but not entirely through the stopper prior to use.

This arrangement helps to retain the stopper in the correct position relative to the penetrating means, reduces the force necessary to completely penetrate the stopper and ensures correct penetration of the stopper.

The invention also provides a medicament delivery kit comprising: (a) a medicament delivery device comprising a housing, a reservoir within the housing, a filling mechanism for the reservoir integral with the housing and means for driving the medicament from the filled reservoir, the filling mechanism being adapted to receive a container for the medicament, said container being sealed by a penetrable stopper, and the filling mechanism comprising means for penetrating the stopper, said penetrating means being in communication with the reservoir to allow the medicament to be transferred from the container to the reservoir via the filling mechanism; and (b) a container sealed by a penetrable stopper which stopper makes a leakproof sliding fit with the interior of the container.

Such a kit is inherently safer and more hygienic than a medicament delivery device which is filled by means of a syringe, as the syringe must first draw in the medicament and subsequently inject it, and this involves the possibilities of contamination of the medicament. Furthermore, it is preferable to eliminate syringes wherever possible because of the dangers associated with contamination or injury by needles.

Suitably, the driving means comprises a gas generating apparatus. According to a preferred embodiment, the gas generating apparatus is in the form of an electrolytic cell. Suitably, the electrolytic cell incorporates a battery.

In an alternative embodiment, the gas generating apparatus comprises two substances which when brought into contact react to generate a gas.

Preferably, the substances are an acid and a base. In a presently preferred embodiment, citric acid and sodium bicarbonate are used, primarily because of their ready reaction and non toxicity, as well as the inert nature of the reaction products (carbon dioxide and water).

According to another embodiment, the driving means comprises a swellable gel. Preferably, the swellable gel swells on contact with a liquid and the driving means further comprises a container containing such a liquid, and means for bringing the liquid and gel into contact.

As indicated above, the medicament may be provided in the form of a solid or semi-solid material which is reconstituted to a liquid form prior to use of the device.

Preferably, in such a case, the medicament is provided as a lyophilised solid.

The invention also provides a medicament delivery device comprising a housing having a skin-contacting surface, a reservoir within the housing, a hollow needle communicating with the reservoir extending, in use, through the periphery of the skin-contacting surface, and driving means for driving a medicament from the reservoir to a patient via the needle.

Disposing a needle on the periphery of the skin contacting surface (i.e. towards the edge of the surface rather than in the central area of the surface) gives rise to a number of advantages in terms of device design and manufacturing costs, and in terms of ease of application of the device to the skin, as will be discussed below.

Suitably, the driving means is located intermediate the reservoir and the skin-contacting surface.

Thus, the driving means is proximal to the skin and is maintained at a temperature close to the skin temperature of the subject. In the same way as the back of a watch is kept at a regular temperature while the temperature of the face of the watch may vary substantially, the driving means of the device according to the invention is maintained at a regular temperature. In general, this increases the accuracy and reliability of the rate at which medicament is driven from the reservoir, leading to an improvement in device safety by providing regular dosing of medicament to the subject.

By having the driving means closer to the skin than the reservoir, it is possible to position the reservoir adjacent the upper surface of the device. By having a transparent or translucent upper surface (or by having a portion of the upper surface which is transparent or translucent), a visual indication can be provided as to the level of medicament in the reservoir. Appropriate shaping of the upper surface allows the volume of drug to be calibrated or, alternatively, allows a simpler indication which merely shows that it is time to replace or refill the device. This prevents a patient from believing that the device is delivering medicament when it is, in fact, empty.

Providing the reservoir at the upper surface of the device and having a transparent upper cover also allows a visual inspection of the medicament. Regulatory authorities often require data sheets to carry a warning such as "Parenteral drug products should be inspected visually for particulate matter and discoloration prior to administration, whenever solution and container permit". This can be achieved using the above configuration.

This configuration provides a further important advantage as it positions the reservoir away from the warmth of the skin, allowing the medicament to be maintained at a lower temperature than in the prior art. If necessary, the reservoir can be thermally insulated to prevent the conduction of heat from the body via the driving means. This allows drugs which are unstable at higher temperatures to be safely used in a device which is to be worn close to the skin.

Thermal insulation of the reservoir may be achieved to any extent desired, i.e. the reservoir can be totally enclosed by an insulating material or only the lower surface of the reservoir (closer to the skin) may be insulated. In many cases the boundary between the reservoir and the driving means is a membrane of some sort, in which case a suitable insulating material can be chosen for use as a membrane.

Preferably, the driving means has a substantially flat configuration and is disposed parallel to the skin-contacting surface.

This arrangement maximises the volume of the driving means which lies close to the skin, assisting in maintaining a regular temperature.

Most preferably, the driving means is located immediately above the skin-contacting surface. As discussed above, the driving means may comprise a gas generating apparatus in the form of an electrolytic cell. The cell preferably comprises upper and lower plates and an electrolytic intermediate said plates, optionally including a battery. This type of cell is easy to manufacture, gives rise to the flat configuration referred to, and may be manufactured cheaply as a self-contained component which is incorporated in a range of medicament delivery devices. If one of the plates is the cathode and the other is the anode, one or both of them may be made of a material which conducts heat efficiently for the reason given above.

In an alternative embodiment, the cell comprises a reservoir for a liquid electrolyte bounded in part by a gas permeable, liquid impermeable membrane, optionally including a battery. The hydrophobic membrane prevents the liquid electrolyte (preferably a diluent electrolyte such as s solution of potassium acetate or dipotassium hydrogen phosphate) from drying out. Such a cell can also be made in a flat configuration and positioned adjacent the skin-contacting surface.

The gas generator may comprise two substances which when brought into contact react to generate a gas, suitably an acid and a base, and in one embodiment, citric acid and sodium bicarbonate.

A gas generator depending on a chemical reaction benefits strongly from being placed proximal to the skin.

In another embodiment, the driving means comprises a swellable gel. Suitably, the swellable gel swells on contact with a liquid and the driving means further comprises a container containing such a liquid, and means for bringing the liquid and gel into contact.

As a rule, any of the above types of driving means (or, indeed, alternative suitable driving means) benefit from having the needle extending through the periphery of the skin-contacting surface, as it allows placement of the driving means intermediate that surface and the reservoir without having a conduit passing through the middle of the driving means, an arrangement which is more difficult and expensive to design and manufacture.

In a preferred embodiment, the skin-contacting surface is in the form of a cover attached to the housing, said cover being movable between first and second positions, the needle being concealed by said cover when the cover is in said first position, and the needle being exposed when the cover is in said second position.

The cover provides a safety feature in a number of ways. Before use, the cover conceals the needle, thereby preventing accidental injury occurring. Additionally, the needle, being concealed, does not pick up any contamination, making it more sterile when it is pierced through the skin. The cover can be moved into the second position by the application of the device to the skin of the subject, so the needle only protrudes when the device has been applied. Upon removal of the device, the cover can be moved back to the first position and thereby concealing the needle and allowing safe disposal of the device or allowing storage of the device for reuse, if this is desired.

Preferably, said cover is mounted on the housing by a hinge mechanism.

Accordingly the cover can be placed against the skin in the first position, with the hinge allowing the device to be pressed towards the skin causing the needle to protrude through the cover and pierce the skin when the cover is in the second position. Preferably, the needle protrudes through the cover at a point distal from the hinge. This makes it easier to pierce the skin with the needle as greater leverage is effected when pushing the housing towards the skin.

Preferably, said cover is provided with a snap mechanism allowing it to snap between said first and second positions. This provides the most effective penetration of the skin, as the snap mechanism causes the needle to jab into the skin quickly (as opposed to the user pressing the needle slowly into and through the skin). The arrangement of a hinge and a snap mechanism provides less traumatic and painful application of the device.

Typical medicaments suitable for use with the device according to the invention include peptides, proteins or hormones such as insulin, calcitonin, calcitonin gene regulating protein, atrial natriuretic protein colony stimulating factor, betaseron, erythropoietin (EPO), interferons such as a, b or g interferon, somatropin, somatotropin, somatostatin, insulin-like growth factor (somatomedins), luteinizing hormone release hormone (LHRH), tissue plasminogen activator (TPA), growth hormone releasing hormone (GHRH), oxytocin, estradiol, growth hormones, leuprolide acetate, factor VIII, interleukins such as interleukin-2, and analogues thereof; analgesics such as fentanyl, sufentanil, butorphanol, buprenorphine, levorphanol, morphine, hydromorphone, hydrocodone, oxymorphone, methodone, lidocaine, bupivacaine, diclofenac, naproxen, paverin, and analogues thereof; anti-migraine agents such as sumatriptan, ergot alkaloids, and analogues thereof; anti-coagulant agents such as heparin, hirudin, and analogues thereof; anti-emetic agents such as scopolamine, ondansetron, domperidone, metoclopramide, and analogues thereof; cardiovascular agents, anti-hypertensive agents and vasodilators such as diltiazem, clonidine, nifedipine, verapamil, isosorbide-5-mononitrate, organic nitrates, agents used in the treatment of heart disorders, and analogues thereof; sedatives such as benzodiazepines, phenothiozines, and analogues thereof; narcotic antagonists such as naltrexone, naloxone, and analogues thereof; chelating agents such as deferoxamine, and analogues thereof; anti-diuretic agents such as desmopressin, vasopressin, and analogues thereof; anti-anginal agents such as nitroglycerine, and analogues thereof; anti-neoplastics such as 5-fluorouracil, bleomycin, and analogues thereof; prostaglandins and analogues thereof; and chemotherapy agents such as vincristine, and analogues thereof.

BRIEF DESCRIPTION OF THE DRAWINGS

The invention will be further illustrated by the following description of embodiments thereof given by way of example only with reference to the accompanying drawings in which.

DETAILED DESCRIPTION OF THE INVENTION

Figure 1:
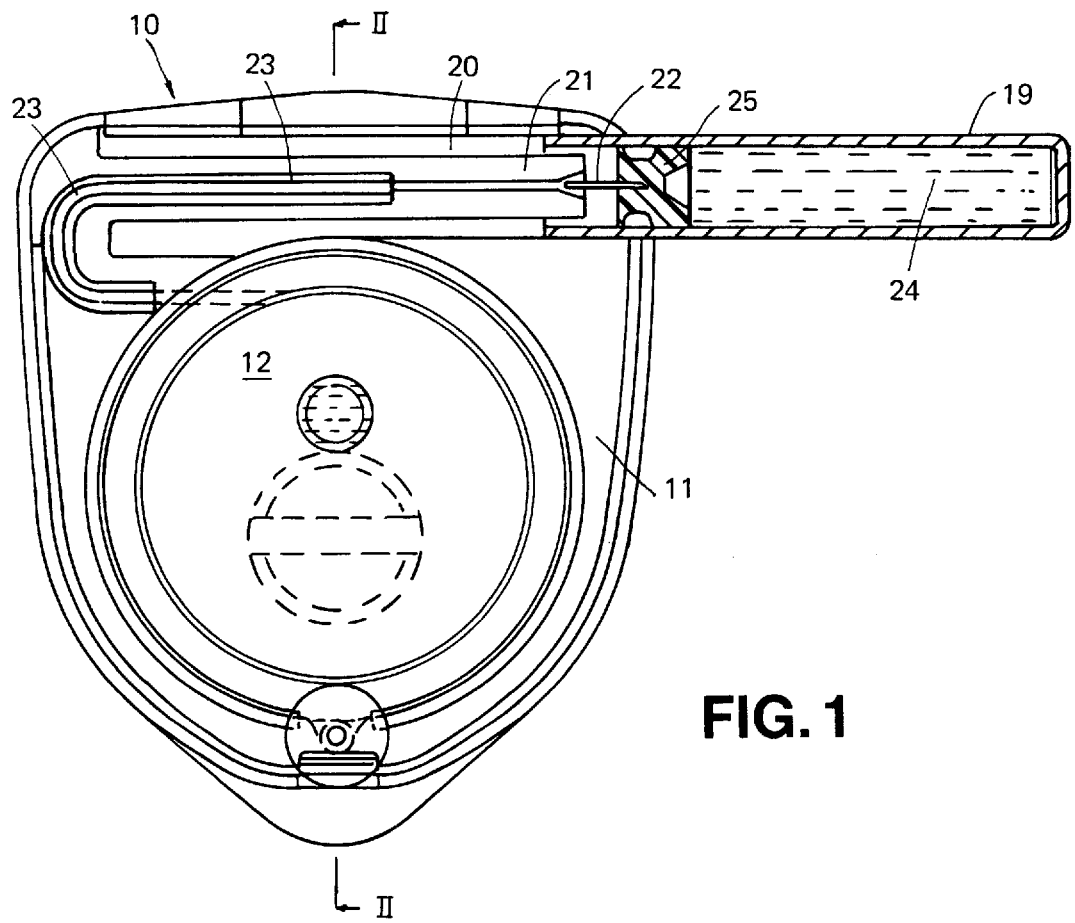
FIG. 1 is a plan view, partially in section, of a device according to the invention, before use.
Figure 2:
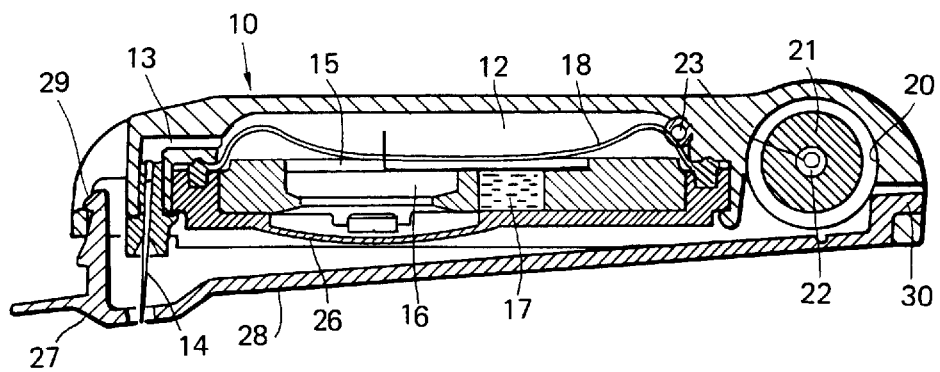
FIG. 2 is a sectional elevation of the device of FIG. 1, taken along the line II—II.

In FIGS. 1 and 2, there is illustrated, generally at 10, a medicament delivery device according to the invention. The device 10 comprises a housing 11 in which there is a reservoir 12 for holding a medicament prior to delivery via a conduit 13 to a hollow delivery needle 14 extending through the periphery of the lower surface of device 10. Needle 14 can effect intradermal, transcutaneous or intramuscular delivery. A gas generator 15 comprising a battery 16 and an electrolyte 17 is used to generate a gas, thereby forcing an elastomeric diaphragm 18 upwards to pressurise the medicament contained in reservoir 12 and expel the medicament through needle 14. The operation of such a device is described in WO 95/13838.

Before use, the reservoir is filled from a container 19 which extends from housing 11 of the device. Housing 11 has an internal bore 20 in which container 19 is slidingly received when pressure is applied to container 19 to press it into housing 11. Bore 20 accommodates an internal rod 21 which acts as a stop and from which a hollow needle 22 projects. Rod 21 has an internal conduit 23 which allows needle 22 to communicate with reservoir 12.

Container 19 is filled with a medicament 24 and sealed by an elastomeric, longitudinally slidable stopper 25. Needle 22, before use, penetrates into but not through elastomeric stopper 25. When container 19 is pressed into bore 20, needle 22 pierces through stopper 25, and then stopper 25 abuts against rod 21. Further movement of container 19 into housing 11 causes stopper 25 to act as a piston (since it remains in position relative to the housing while cylindrical container 19 moves into the housing). This causes the medicament 24 to be compressed and to be expelled from container 19 via needle 22 and conduit 23 into reservoir 12. A filter (not shown) in the conduit serves as a safety precaution to remove the possibility of accidental contamination of the medicament by solid particles.

Container 19 is assembled integrally with housing 11, and is supplied to the patient as shown in FIGS. 1 and 2. It will be appreciated that all that is required to fill the reservoir from sterile, sealed container 19 is to press container 19 into bore 20 in housing 11. Throughout the process, i.e. before, during and after use, needle 22 remains hidden. Thus, device 10 (including container 19) can be safely disposed of without a danger of injury or misuse.

The operation of the device will now be described. Gas generator 15 is actuated by means of a switch 26 adjacent to a base cover 27 as hereafter described. Base cover 27 conceals delivery needle 14 before use. The lower surface 28 of base cover 27 is coated with an adhesive. When it is desired to use the device (i.e. after container 19 has been depressed into housing 11 to fill reservoir 12), device 10 is pressed against and adheres to the skin. A snap mechanism 29 allows cover 27 to snap upwards under the applied pressure, as cover 27 is attached to housing 11 of device 10 by means of a hinge 30. Needle 14 punctures the skin as a result of this snap action, and cover 27 actuates switch 26, thereby causing the generation of gas and the subsequent delivery of medicament from reservoir 12 via conduit 13 and delivery needle 14 to the patient.

It will be appreciated that snap mechanism 29 and hinge 30 are more efficient than a snap mechanism where the entire device must snap onto a cover. A good deal less force is required to snap the cover into place where a hinge acting as a fulcrum is used. This makes the application of the device less forceful which should aid patient compliance and acceptance. Furthermore, because needle 14 is located on the periphery of the surface defined by cover 27, it travels approximately twice as quickly when cover 27 snaps shut as it would if it were located in the centre of the device (i.e.

twice as close to the hinge). This leads to a less traumatic and less painful puncturing of the skin, since experience shows that a needle jabbed quickly into the skin hurts less than a needle which is slowly pressed into the skin.

Figure 3:
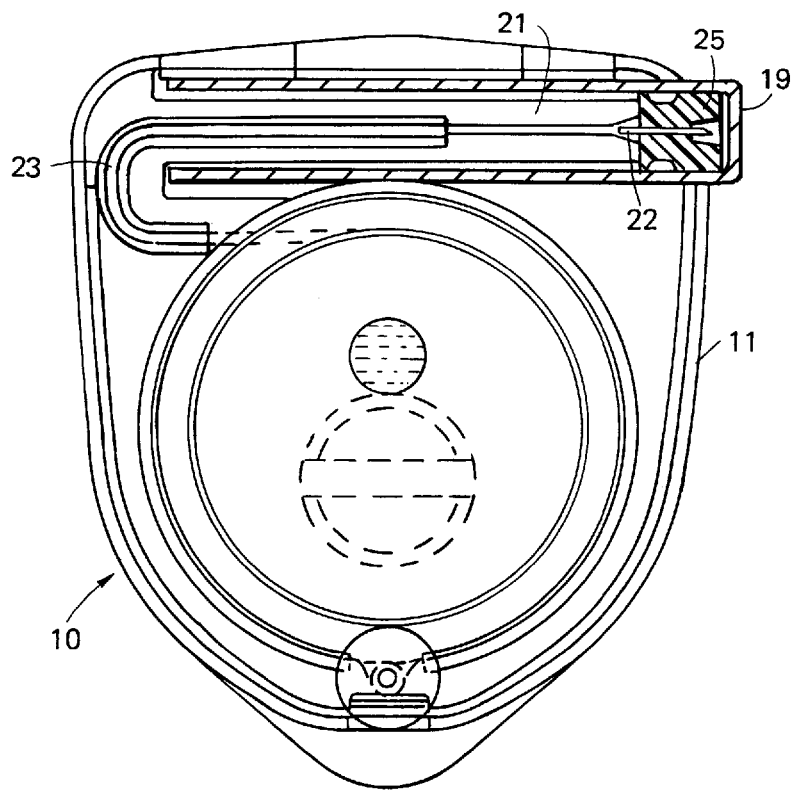
FIG. 3 shows the device as illustrated in FIG. 1, when in use.
Figure 4:
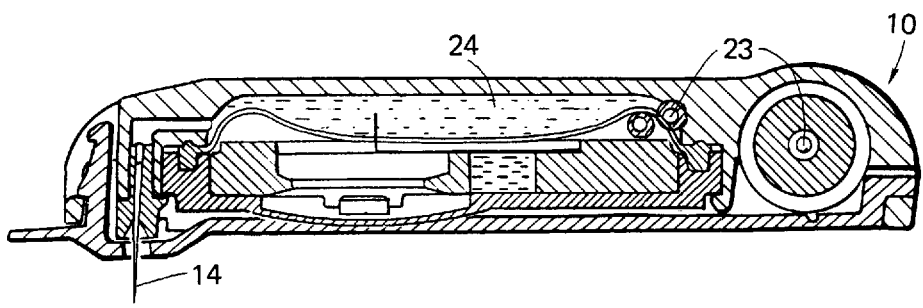
FIG. 4 shows the device as illustrated in FIG. 2, when in use.

FIGS. 3 and 4 show device 10 of FIGS. 1 and 2, when in use. Thus, it can be seen that container 19 is fully depressed into housing 11, and stopper 25, being held in position by rod 21, has moved through the length of container 19, thereby completely emptying container 19 of the medicament. The medicament 24 has been discharged via needle 22 and internal conduit 23 into reservoir 12 (FIG. 4).

As device 10 has been pressed against the patient's skin, base cover 27 has snapped upwards, exposing needle 14 and allowing delivery of medicament 24 within reservoir 12 through the skin.

Figure 5:
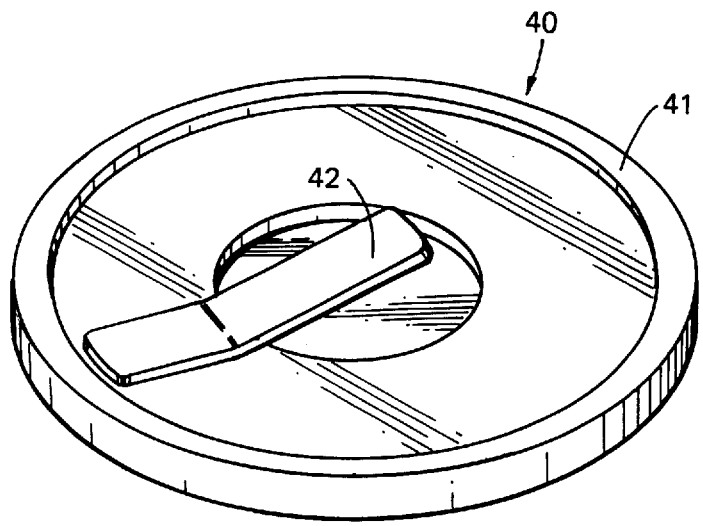
FIG. 5 is a perspective view of the gas generator of the device illustrated in FIGS. 1–4.
Figure 6:
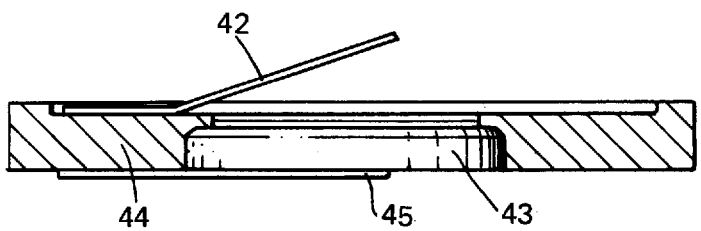
FIG. 6 is a sectional elevation of the gas generator shown in FIG. 5.

FIGS. 5 and 6 show the gas generator of the device of FIGS. 1–4 in greater detail. FIG. 5 shows that the generator, illustrated generally at 40, is in the form of a circular disc 41 having a flexible raised contact 42 extending therefrom. In FIG. 6, it can be seen that the generator comprises a battery 43 and an electrolyte 44, the electrolyte being contacted on one side by a cathode 45 extending from the battery 43, and on the other side by an anode, in the form of contact 42. It will be appreciated that the gas generator as illustrated does not generate gas until contact 42 has been depressed to touch battery 43, thereby completing the circuit. Thus, when the gas generator is incorporated (in inverted position) into the device illustrated in FIGS. 1–4, gas generation only begins when base cover 27 (see FIGS. 2 and 4) has snapped upwards as the device 10 is pressed against the patient's skin.

When gas generator 40 is incorporated in device 10, it lies parallel to the skin-contacting surface. The substantially flat configuration of generator 40 maximises the surface area and volume of the generator lying near the skin. It can be seen from FIGS. 2 and 4 that the internal components of the device 10 are arranged to have the gas generator intermediate the reservoir and the skin, in a reversal of the conventional configuration. It has been found that the configuration shown in FIGS. 2 and 4 is, however, preferable as the electrolytic cell remains at a temperature very close to the skin temperature. Once calibrated, the rate of gas generation and hence delivery of drug, can be reliably predicted and utilised. Not only does the rate of gas generation vary less, but the volume of gas below membrane 18 also fluctuates less.

The positioning of needle 14 at the periphery of skin-contacting surface 27 allows this configuration to be exploited using the cheap and simple electrolytic cell of FIGS. 5 and 6. Generally, positioning the cell between the reservoir and the skin would be expected to involve a design of electrolytic cell which allows a conduit to pass therethrough from the reservoir to the needle. This can be effected if necessary, but if it is desired to use a separately produced cell for subsequent inclusion in the device, then the cell must have an awkward design such as an annular design. This problem is overcome by offsetting the needle from the side of the reservoir to extend through the periphery of the skin-contacting surface. This arrangement is advantageous not only with electrolytic cells and other gas generators but also with any type of temperature dependent driving means.

Figure 7:
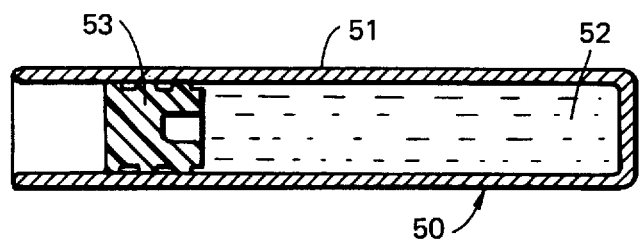
FIG. 7 is a longitudinal sectional view of a container adapted for use in the present invention.

FIG. 7 illustrates a container for use with the device according to the invention. The container, illustrated generally at 50, comprises a container body 51 in the form of a glass vial containing a medicament 52 and sealed by a penetrable elastomeric stopper 53. Container 50 can be sold separately from a device such as that illustrated in FIGS. 1–4, or it can be sold in kit form with the device according to the invention. In FIGS. 1–4, the device is shown as it would be sold in a preferred embodiment, with the container pre-mounted on the device. This is not, however, the only way of supplying the device; a single type of device could be sold together with a wide choice of containers in the form of container 50, each different container having a different type of medicament or a different medicament strength.

Figure 8:
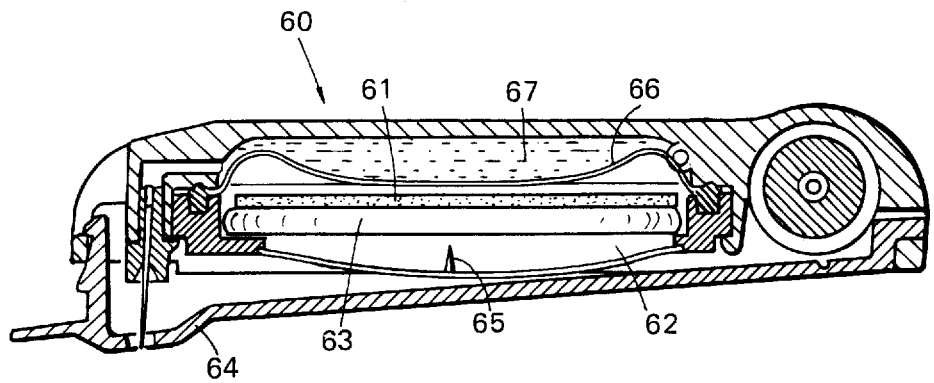
FIG. 8 is a sectional elevation of a second embodiment of a medicament delivery device according to the invention.
Figure 9:
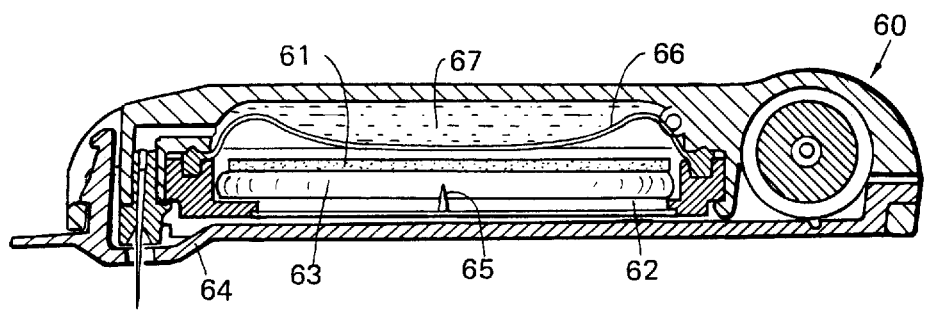
FIG. 9 shows the device as illustrated in FIG. 8 in use.

FIG. 8 illustrates a second embodiment of a device according to the invention. The device, indicated generally at 60 is in many respects similar to the device illustrated in FIGS. 1–4, except a different driving means is used to deliver medicament. The driving means comprises a swellable gel 61 located in a compartment 62 together with a pierceable water container 63. Referring to FIG. 9, it can be seen that when device 60 is applied and adheres to the skin, a cover 64 snaps upwards and causes a needle 65 to pierce container 63, releasing water and thereby wetting gel 61, which causes gel 61 to swell, and thereby displace a membrane 66 to effect delivery of medicament from reservoir 67 in a similar manner to the delivery effected by the generation of gas in the device of FIGS. 1–4.

Another embodiment of the invention has the same configuration illustrated in FIGS. 8 and 9 but gel 61 is replaced by sodium bicarbonate and container 63 contains a citric acid solution rather than water. When container 63 is pierced as cover 64 snaps upwards, citric acid is released into contact with sodium bicarbonate, thereby generating carbon dioxide to drive medicament from the reservoir.

The embodiment having a swellable gel is preferred for a slow release of medicament over, for example, 12, 24 or 48 hours. The embodiment having an acid and a base is suitable for rapid delivery. Such delivery may empty the reservoir in 20 minutes or less, if desired.

Figure 10:
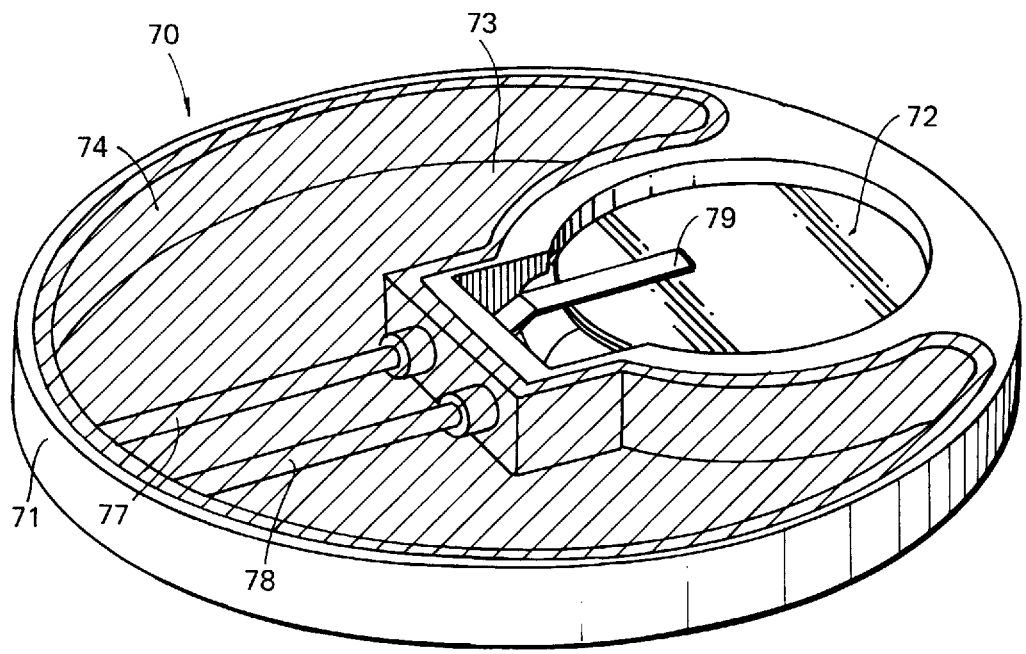
FIG. 10 is a perspective view of a gas generator for use in a device according to the invention.
Figure 11:
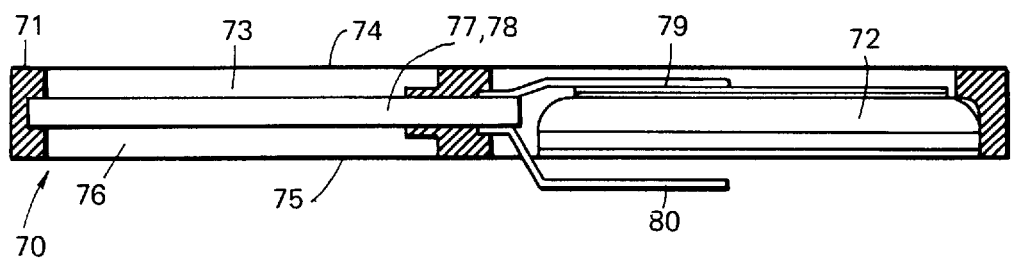
FIG. 11 is a sectional elevation of the generator of FIG. 10.

FIGS. 10 and 11 illustrate an alternative electrolytic cell to that shown in FIGS. 5 and 6. The cell, indicated generally at 70, comprises a flat cylindrical housing 71 incorporating a battery 72 and an electrolyte reservoir 73. Reservoir 73 is enclosed above and below by a pair of hydrophobic membranes 74,75 which are gas permeable and liquid impermeable.

Reservoir 73 is filled with a diluent electrolyte, such as an aqueous solution of potassium acetate ($CH_3COOK$) 76. Alternative electrolytes, such as a solution of dipotassium hydrogen phosphate ($K_2HPO_4$), will be known to the skilled person. Hydrophobic membranes 74,75 prevent electrolyte 76 from drying out during extended storage, but allow the release of gas from reservoir 73.

A cathode 77 and an anode 78 extend through reservoir 73 and generate a gas when connected to the terminals of battery 72 by a pair of contacts 79,80. Contact 80 (see FIG. 11) must be pressed against battery 72 to complete the circuit, and this is suitably effected by snapping a cover closed as described above.

Different combinations of driving means can be employed. Thus, basal delivery rates can be achieved by having a swellable gel or electrolytic cell, combined with one or more acid/base compartments for rapid delivery of medicament by the depression of a button causing a needle to pierce a compartment. This type of arrangement may be suitable where the device is used for patient-controlled analgesia, i.e. delivering a constant low dosage of pain-killer with short bursts of stronger relief.

Figure 12:
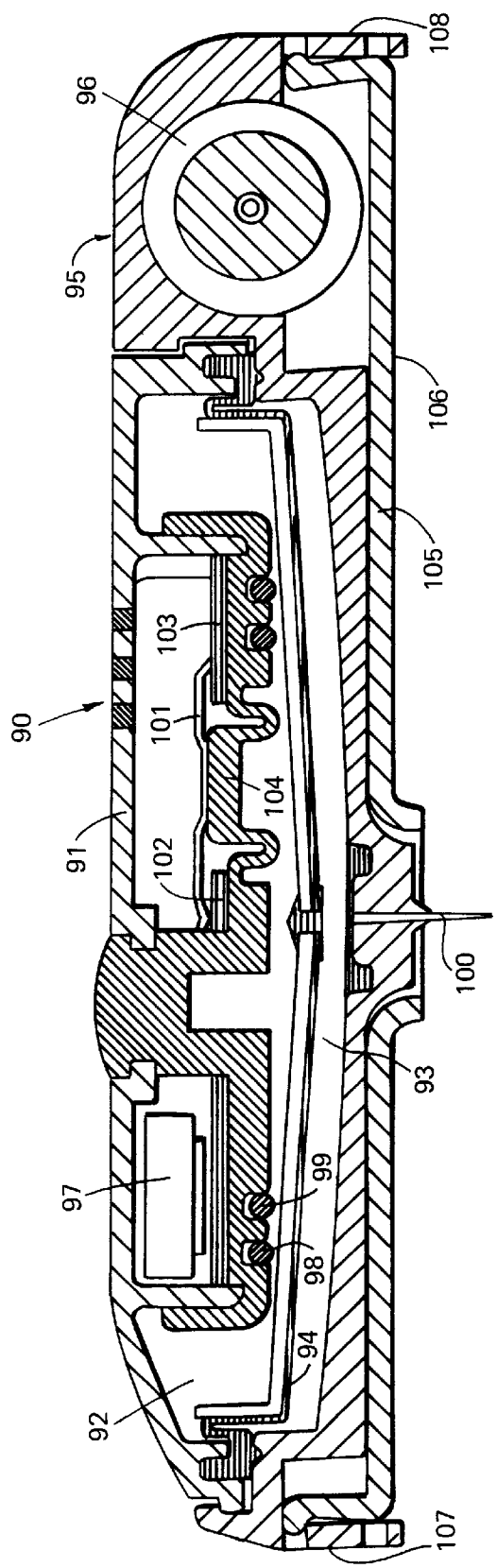
FIG. 12 is a sectional elevation of a third embodiment of a liquid delivery device according to the invention.

In FIG. 12, there is indicated, generally at 90, a further embodiment of liquid delivery device according to the invention. The device comprises a housing 91 having a gas generation compartment 92 and a medicament reservoir 93. Compartment 92 and reservoir 93 are separated by an elastomeric diaphragm 94. Reservoir 93 is in communication with a filling mechanism, indicated generally at 95, identical to the filling mechanism described in detail in relation to FIGS. 1–4. Thus, it comprises an internal bore 96 for receiving a cylindrical container which may be supplied integrally with device 90 or may be supplied separately. In cases where it is supplied separately, bore 96 can be covered before use by a sterile elastomeric tab such as a Tyrax tab (Tyrax is a Trade Mark), the tab being peeled off before use to allow access to the bore, at which point a container such as the container illustrated in FIG. 7 is introduced into the bore and pushed home as previously described.

Gas generation chamber 92 contains an electrolytic cell which basically comprises a battery 97 communicating with a cathode 98 and an anode 99, chamber 92 being filled with an electrolyte. Upon actuation of the cell, a current flows between cathode 98 and anode 99 via the electrolyte, thereby generating a gas which forces diaphragm 94 downwards to eject a medicament from reservoir 93 via hollow needle 100. The electrolytic cell is also provided with a bridging contact 101 which forms part of the electric circuit between two fixed contacts 102,103. Bridging contact 101 is mounted on a switch diaphragm 104. If the needle 100 is occluded or reservoir 93 becomes emptied, the pressure increases within gas generation chamber 92 causing switch diaphragm 104 to lift upwards, thereby breaking the electrical circuit between contacts 102,103. This is used as a safety feature to prevent continued generation of gas when delivery is completed or the needle 100 is occluded.

It will be noted that device 90 is provided with a displaceable cover 105 which is provided with an adhesive undersurface 106 for attachment to the skin of the subject. Unlike the devices of FIGS. 1–4 and FIGS. 8 and 9, cover 105 is not mounted via a hinge mechanism, but instead is provided with snap mechanisms 107,108, both of which snap to the position shown in FIG. 12 when device 90 is applied to and pressed against the skin.

It will also be noticed that needle 100 is mounted substantially in the centre of the base of device 90, and not on the periphery of the lower surface. Although this is presently less preferred (since a needle located on the periphery of the lower surface gives rise to a number of advantages, as described above), it nevertheless illustrates that filling mechanism 95 can be integrated into a wide range of medicament delivery devices, including device 90 which is adapted from the device described in WO 95/13838. Whereas the device described in WO 95/13838 had to be prefilled with medicament or filled with a syringe via an injection port immediately prior to use, thereby giving rise to the disadvantages set out above, device 90, being provided with filling mechanism 95, is easier to use, safer and more hygienic than prior art devices.

In an alternative embodiment, cover 105 is mounted on housing 91 by means of a screw thread which replaces the snap mechanisms 107,108. Thus, cover 105 is applied to and adheres to the skin and housing 91 is rotated relative to cover 105, the screw thread causing the cover to be drawn towards the housing, and thereby causing the needle to extend through the cover and pierce the skin. Optionally, a switch can be activated when the housing and cover approach one another, thereby beginning delivery of medicament when the needle has penetrated the skin.

What is claimed is:

1. A medicament delivery device comprising a housing, a reservoir within the housing, a filling mechanism for the reservoir integral with the housing and gas generated means for driving the medicament from the filled reservoir, the filling mechanism being adapted to receive a container for the medicament, said container being sealed by a penetrable stopper, and the filling mechanism comprising means for penetrating the stopper, said penetrating means being in communication with the reservoir to allow the medicament to be transferred from the container to the reservoir via the filling mechanism.

2. A medicament delivery device according to claim 1, wherein the medicament is provided in the form of a solid material which is reconstituted to a liquid form prior to use of the device.

3. A medicament delivery device according to claim 2, wherein the medicament is provided as a lyophilised solid.

4. A medicament delivery device according to claim 3, wherein a portion of the housing is transparent or translucent thereby allowing visual inspection of the reservoir contents.

5. A medicament delivery device according to claim 4, wherein said cover is provided with a snap mechanism allowing it to snap between a first and a second position.

6. A medicament delivery device according to claim 1, wherein the housing has a skin-contacting surface, and further comprising a hollow needle communicating with the reservoir extending, in use, through the periphery of the skin-contacting surface.

7. A medicament delivery device according to claim 6, wherein the driving means is located intermediate the reservoir and the skin-contacting surface.

8. A medicament delivery device according to claim 7, wherein the driving means has a substantially flat configuration and is disposed parallel to the skin-contacting surface.

9. A medicament delivery device according to claim 6, wherein the skin-contacting surface is in the form of a cover attached to the housing, said cover being movable between first and second positions, the needle being concealed by said cover when the cover is in said first position, and the needle being exposed when the cover is in said second position.

10. A medicament delivery device according to claim 9, wherein said cover is mounted on the housing by a hinge mechanism.

11. A medicament delivery device according to claim 6, wherein the driving means is located immediately above the skin-contacting surface.

12. A medicament delivery device according to claim 1, wherein the gas generating apparatus is in the form of an electrolytic cell.

13. A medicament delivery device according to claim 12, wherein the electrolytic cell comprises upper and lower plates and an electrolyte intermediate said plates.

14. A medicament delivery device according to claim 13, wherein the electrolytic cell further comprises a battery.

15. A medicament delivery device according to claim 12, wherein the electrolytic cell comprises a reservoir for a liquid electrolyte bounded in part by a gas permeable, liquid impermeable membrane.

16. A medicament delivery device according to claim 15, wherein the electrolytic cell further comprises a battery.

17. A medicament delivery device according to claim 1, wherein the housing is provided with a bore which receives the container and the penetrating means is disposed on a stop within the bore, such that the stopper is penetrated and abuts against the stop when the container is pushed along the bore, the penetrated stopper acting as a piston to deliver the medicament from the container.

18. A medicament delivery device according to claim 17, wherein the penetrating means comprises a hollow needle and the stop is a rod extending within the bore, the needle communicating with the reservoir via a conduit extending internally of the rod.

19. A medicament delivery device according to claim 1, wherein the gas generating apparatus comprises two substances which when brought into contact react to generate a gas.

20. A medicament delivery device according to claim 19, wherein the substances are an acid and a base.

21. A medicament delivery device according to claim 1, wherein the driving means comprises a swellable gel.

22. A medicament delivery device according to claim 21, wherein the swellable gel swells on contact with a liquid and the driving means further comprises a container containing such a liquid, and means for bringing the liquid and gel into contact.

23. A medicament delivery device according to claim 1, wherein the container protrudes from the housing prior to use and moves to a recessed position within the housing when the reservoir is filled with the medicament.

24. A medicament delivery device according to claim 1, wherein the container is integral with the housing.

25. A medicament delivery device according to claim 1, wherein the container is separate from the housing and is mounted thereon prior to use.

26. A medicament delivery device according to claim 1, wherein the penetrating means penetrates partially into but not entirely through the stopper prior to use.

27. A medicament delivery device according to claim 1, wherein the medicament is selected from peptides, proteins, hormones, analgesics, anti-migraine agents, anti-coagulant narcotic antagonists, chelating agents, anti-anginal agents, chemotherapy agents, sedatives, anti-neoplastics, protaglandins and antidiuretic agents.

28. A medicament delivery device according to claim 1, wherein the medicament is provided in the form of a semi-solid material which is reconstituted to a liquid form prior to use of the device.

29. A medicament delivery device comprising a housing having a skin-contacting surface, a reservoir within the housing, a hollow needle, in hinged relation to the housing, communicating with the reservoir extending, in use, through the periphery of the skin-contacting surface, and driving means for driving a medicament from the reservoir to a patient via the needle.

30. A medicament delivery device according to claim 29, wherein the driving means comprises a gas generating apparatus.

31. A medicament delivery device according to claim 30, wherein the gas generating apparatus is in the form of an electrolytic cell.

32. A medicament delivery device according to claim 31, wherein the electrolytic cell comprises upper and lower plates and an electrolyte intermediate said plates.

33. A medicament delivery device according to claim 32, wherein the electrolytic cell further comprises a battery.

34. A medicament delivery device according to claim 31, wherein the electrolytic cell comprises a reservoir for a liquid electrolyte bounded in part by a gas permeable, liquid impermeable membrane.

35. A medicament delivery device according to claim 34, wherein the electrolytic cell further comprises a battery.

36. A medicament delivery device according to claim 30, wherein the gas generating apparatus comprises two substances which when brought into contact react to generate a gas.

37. A medicament delivery device according to claim 36, wherein the substances are an acid and a base.

38. A medicament delivery device according to claim 29, further comprising a filling mechanism for the reservoir integral with the housing, the filling mechanism being adapted to receive a container for the medicament, said container being sealed by a penetrable stopper, and the filling mechanism comprising means for penetrating the stopper, said penetrating means being in communication with the reservoir to allow the medicament to be transferred from the container to the reservoir via the filling mechanism.

39. A medicament delivery device according to claim 38, wherein the container is capable of sliding within the housing, and the stopper makes a leakproof sliding fit with the interior of the container.

40. A medicament delivery device according to claim 39, wherein the housing is provided with a bore which receives the container and the penetrating means is disposed on a stop within the bore, such that the stopper is penetrated and abuts against the stop when the container is pushed along the bore, the penetrated stopper acting as a piston to deliver the medicament from the container.

41. A medicament delivery device according to claim 40, wherein the penetrating means comprises a hollow needle and the stop is a rod extending within the bore, the needle communicating with the reservoir via a conduit extending internally of the rod.

42. A medicament delivery kit comprising:
    (a) A medicament delivery device according to claim 38; and
    (b) a container sealed by a penetrable stopper which stopper makes a leakproof sliding fit with the interior of the container.

43. A medicament delivery device according to claim 42, wherein the medicament is selected from peptides, proteins, hormones, analgesics, anti-migraine agents, anti-coagulant narcotic antagonists, chelating agents, anti-anginal agents, chemotherapy agents, sedatives, anti-neoplastics, protaglandins and antidiuretic agents.

44. A medicament delivery device according claim 38, wherein the container is integral with the housing.

45. A medicament delivery device according claim 38, wherein the container is separate from the housing and is mounted thereon prior to use.

46. A medicament delivery device according to claim 38, wherein the container protrudes from the housing prior to use and moves to a recessed position within the housing when the reservoir is filled with the medicament.

47. A medicament delivery device according to claim 38, wherein the penetrating means penetrates partially into but not entirely through the stopper prior to use.

48. A medicament delivery device according to claim 29, wherein the driving means is located intermediate the reservoir and the skin-contacting surface.

49. A medicament delivery device according to claim 48, wherein the driving means has a substantially flat configuration and is disposed parallel to the skin-contacting surface.

50. A medicament delivery device according to claim 49, wherein the driving means is located immediately above the skin-contacting surface.

51. A medicament delivery device according to claim 29, wherein the driving means comprises a swellable gel.

52. A medicament delivery device according to claim 51, wherein the swellable gel swells on contact with a liquid and the driving means further comprises a container containing such a liquid, and means for bringing the liquid and gel into contact.

53. A medicament delivery device according claim 29, wherein the medicament is provided in the form of a solid material which is reconstituted to a liquid form prior to use of the device.

54. A medicament delivery device according to claim 53, wherein the medicament is provided as a lyophilised solid.

55. A medicament delivery device according to claim 29, wherein the skin-contacting surface is in the form of a cover attached to the housing, said cover being movable between first and second positions, the needle being concealed by said cover when the cover is in said first position, and the needle being exposed when the cover is in said second position.

56. A medicament delivery device according to claim 55, wherein said cover is mounted on the housing by a hinge mechanism.

57. A medicament delivery device according to claim 56, wherein said cover is provided with a snap mechanism allowing it to snap between said first and second positions.

58. A medicament delivery device according to claim 55, wherein said cover is provided with a snap mechanism allowing it to snap between said first and second positions.

59. A medicament delivery device according claim 29, wherein a portion of the housing is transparent or translucent thereby allowing visual inspection of the reservoir contents.

60. A medicament delivery device according to claim 29, wherein the medicament is selected from peptides, proteins, hormones, analgesics, anti-migraine agents, anti-coagulant narcotic antagonists, chelating agents, anti-anginal agents, chemotherapy agents, sedatives, anti-neoplastics, protaglandins and antidiuretic agents.

61. A medicament delivery device according to claim 29, wherein the medicament is provided in the form of a semi-solid material which is reconstituted to a liquid form prior to use of the device.

62. A medicament delivery kit comprising:
  (a) a medicament delivery device comprising a housing, a reservoir within the housing, a filling mechanism for the reservoir integral with the housing and gas generated means for driving the medicament from the filled reservoir, the filling mechanism being adapted to receive a container for the medicament, said container being sealed by a penetrable stopper, and the filling mechanism comprising means for penetrating the stopper, said penetrating means being in communication with the reservoir to allow the medicament to be transferred from the container to the reservoir via the filling mechanism; and
  (b) a container sealed by a penetrable stopper which stopper makes a leakproof sliding fit with the interior of the container.

63. A medicament delivery kit according to claim 62, wherein the medicament is selected from peptides, proteins, hormones, analgesics, anti-migraine agents, anti-coagulant narcotic antagonists, chelating agents, anti-anginal agents, chemotherapy agents, sedatives, anti-neoplastics, protaglandins and antidiuretic agents.

* * * * *